United States Patent [19]

Smesny

[11] Patent Number: 5,269,999
[45] Date of Patent: Dec. 14, 1993

[54] PREPARATION OF CORE SAMPLES

[75] Inventor: Mark A. Smesny, Richland Hills, Tex.

[73] Assignee: Gas Research Institute, Chicago, Ill.

[21] Appl. No.: 860,974

[22] Filed: Mar. 31, 1992

[51] Int. Cl.$^5$ ............................................. B29C 43/02
[52] U.S. Cl. ..................................... 264/570; 264/112; 264/118
[58] Field of Search ................ 264/112, 113, 118, 570; 73/153

[56] References Cited

U.S. PATENT DOCUMENTS

| | | | |
|---|---|---|---|
| 2,662,401 | 12/1953 | Bailly | 73/153 |
| 3,882,215 | 5/1975 | Dyke et al. | 264/113 |
| 4,009,239 | 2/1977 | Bowen | 264/112 |
| 4,799,382 | 1/1989 | Sprunt et al. | 73/153 |
| 4,916,945 | 4/1990 | Weisbrod | 73/153 |
| 5,079,948 | 1/1992 | Collins | 73/153 |

OTHER PUBLICATIONS

Daniel J. Soeder; "Applications of Fluorescence Microscopy to Study of Pores in Tight Rocks"; *American Association of Petroleum Geologists* Bulletin, vol. 74, No. 1 (Jan. 1990), pp. 30–40, 9 Figs.

L. A. Hyman et al.; "The Effects of Microfractures on Directional Permeability in Tight Gas Sands"; SPE #21878, presented at the SPE Rocky Mountain Regional/Low Permeability Reservoirs Symposium & Exhibition, Apr. 15–17, 1991.

*Primary Examiner*—Mary Lynn Theisen
*Attorney, Agent, or Firm*—Arnold, WHite & Durkee

[57] ABSTRACT

A system is disclosed for impregnating a stack of low permeability core samples with epoxy resin, preferably containing fluorescent dye. The system is particularly suited for preparing core samples from tight gas sands for thin section analysis. The system creates channels through which the epoxy can flow, thereby avoiding the problems of prior methods where uppermost samples in a stack prohibit epoxy flow from reaching lowermost samples in the stack. In the practice of this invention, the core samples are alternately layered with a highly permeable material such as a synthetic material comprised of silica sand bonded with aluminum silica glass. The resulting stack is encapsulated in heat shrink tubing with coarse sand positioned between the outer walls of the stack and the inner walls of the tubing. After the tubing is heat shrunk around the stack, the stack is placed in an overburden coreholder for introduction of epoxy into the core samples under increasing pressure. After the epoxy has hardened, the stack of cores may be removed from the coreholder and separately recovered.

12 Claims, 1 Drawing Sheet

PREPARATION OF CORE SAMPLES

FIELD OF THE INVENTION

This invention relates to a system for preparing samples of reservoir rock and sands for analysis, particularly thin section analysis employing dye The system of the invention is especially suited to preparing a plurality of such samples at the same time.

BACKGROUND OF THE INVENTION

In the oil and gas industry, core samples taken from oil and gas reservoirs are commonly analyzed to determine or measure various characteristics of the reservoir. Such analysis may include viewing thin sections of the core samples under a microscope. To enable core samples of unconsolidated reservoir sands to be sliced for thin section analysis, such core samples are typically impregnated with epoxy resin. Known methods for impregnating such sands with epoxy resin, however, are problematic when the sands have relatively low permeability, as typically seen with tight gas sands. The low permeability of the sample results in restricted flow of the epoxy resin-former, such that the epoxy fails to penetrate the entire sample or to flow from one sample to another in a stack of samples being prepared. Improved methods are needed for impregnating low permeability sands with epoxy.

SUMMARY OF THE INVENTION

This invention is particularly suited for preparing samples of reservoir sands of low permeability, such as tight gas sands commonly found in the oil and gas industry, for thin section analysis In the invention, core samples are alternated in a stack with highly permeable material, such as, for example, a synthetic material comprised of silica sand bonded with aluminum or alumina silica glass. The stack is then preferably positioned in heat shrink tubing, with highly permeable material on each end and with coarse sand or other suitable, highly permeable material between the outer walls of the stack and the inner walls of the tubing. The tubing is shrunk to encompass the stack and the stack is then placed into a coreholder. Epoxy or other suitable resin-former, preferably containing dye, particularly fluorescent dye, is introduced into the stack under increasing pressure. The epoxy flows through the sand and the highly permeable material where it enters the core samples. The epoxy is allowed to harden in the stack before removing the stack from the coreholder.

Upon removal of the stack from the coreholder, the tubing and sand may be cut away so that the core samples may be separated from the highly permeable material and so that thin sections of the core samples may be cut for analysis

DESCRIPTION OF THE PREFERRED EMBODIMENT

Figure 1:
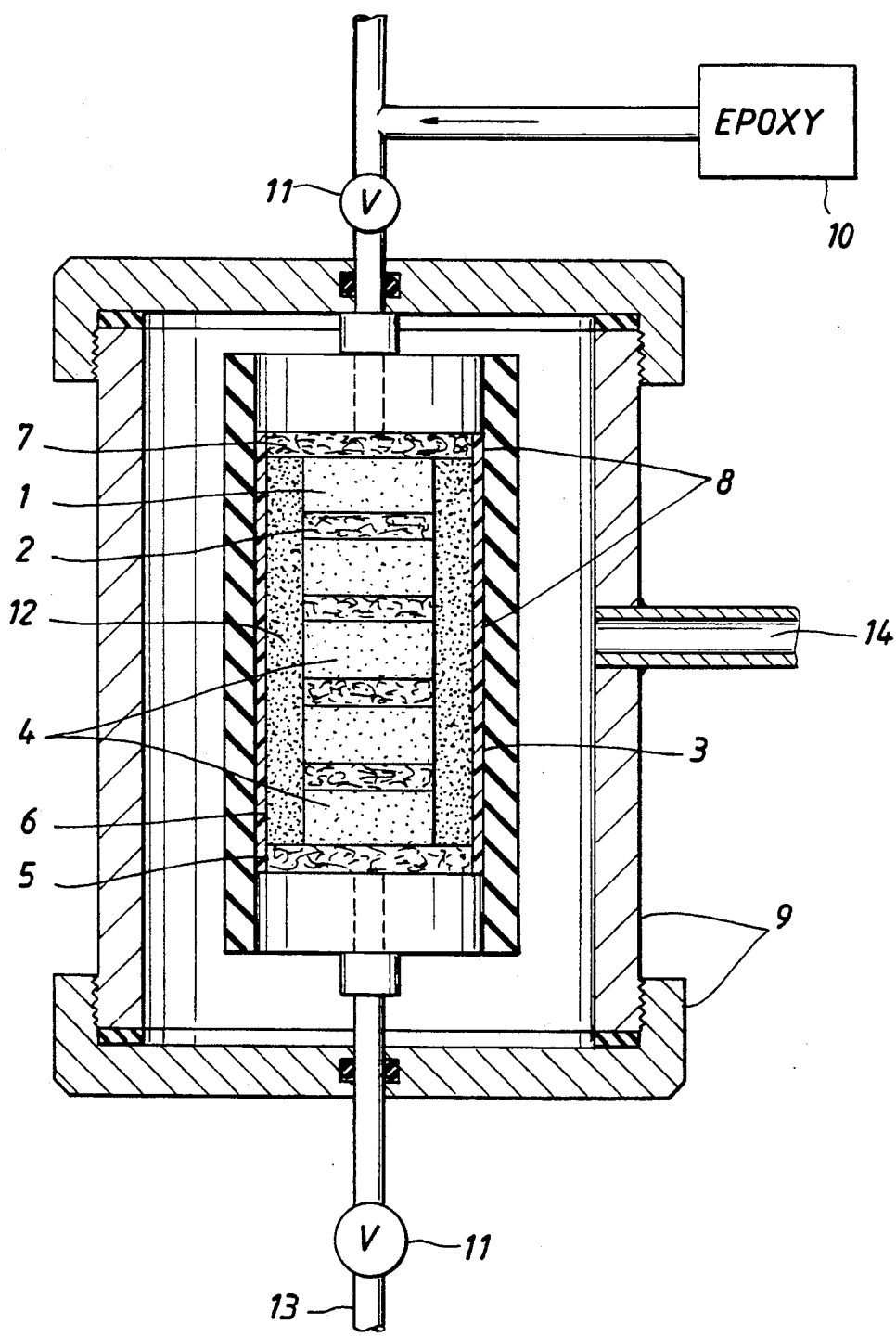
FIG. 1 is a schematic of a stack of core samples, prepared according to the method of this invention and positioned in an overburden coreholder for impregnation with epoxy resin.

A system is disclosed for impregnating reservoir core samples with epoxy or other suitable monomer or copolymer capable of forming a solid resin. The system is particularly suited for impregnating a stack of core samples taken from tight gas sands or other low permeability reservoirs.

In practicing the invention, cores are cut from samples taken from the reservoir. Typically, such cores are taken by drilling out from the samples vertical plugs, which may also be called core samples, usually about one inch in diameter and about one-fourth inch in thickness. Notches may be made in the plugs to indicate the direction of the sample as taken from the reservoir provided the samples were originally taken from the reservoir with the direction noted. For example, a large notch might indicate north and a smaller notch east. Plugs may be drilled or notched from any direction according to the type of orientation desired.

Referring to FIG. 1, plugs 1 are dried and then stacked alternately with a highly permeable material 2, such as filtrose, a synthesized material of silica sand bonded with aluminum or alumina silica glass. Filtrose has a permeability of about 10–12 darcies and a porosity of about 35–40%. This highly permeable material 2 between the plugs is preferably about one inch in diameter and about one-eighth inch in thickness, or generally about the same diameter as the plugs but with less thickness. The stack 4 of plugs and filtrose or other highly permeable material is then preferably rolled in paper for ease of handling.

An amount or disk 5 of filtrose or other highly permeable material, preferably about one and one-half inches in diameter and about one-eighth inch in thickness, or generally of greater diameter than the plugs but with less thickness, is placed into one end of heat shrink tubing 3. The tubing 3 should be of sufficient length and width as to be able to extend the length of the stack 4 and fully encompass the stack. Heat shrink tubing may be comprised of any material which shrinks when exposed to heat, particularly polymeric materials, such as, for example, polytetrafluoroethylene, fluorinated ethylene/propylene copolymer, polytetrafluoroethylene with perfluoroalkoxy side chains, polyvinylidene fluoride and mixtures thereof.

One end of the stack 4 is placed on the disk 5 so that the stack 4 is centered within the heat shrink tubing 3. Coarse sand 12, about 16-20 mesh, or other suitable particulate material, is packed between the stack 4 and the inner wall 6 of the heat shrink tubing 3 up to and about level with the top of the stack 4. The paper is removed from about the stack 4, preferably without disturbing the stack. An amount or disk 7 of filtrose or other highly permeable material, preferably about one and one-half inches in diameter and about one-eighth inch in thickness, or generally of greater diameter than the plugs but with less thickness, is placed on top of the stack 4 inside the heat shrink tubing 3.

The tubing 3 is shrunk with the ends of the tubing flush with the outer surfaces of the disks 5 and 7, forming a capsule 8. A heating means or heater, e.g., a heating gun, is preferably used to shrink the tubing so that the tubing fits tightly about the stack. After the tubing is shrunk about the stack, the capsule is ready for further processing, particularly impregnation of epoxy, preferably containing dye, into the plugs.

One manner for accomplishing such impregnation is to place the capsule 8, comprising the stack of plugs surrounded or encompassed by tubing, into an overburden coreholder 9, such as a Hassler-type coreholder, with a rubber boot for holding the stack, as is commonly used in the oil and gas industry for core preparation and reservoir analysis. The capsule, or the plugs within the capsule, are evacuated for several hours, employing vacuum 13 from a vacuum source, after which hydrostatic overburden pressure 14 is applied to the outer boot of the coreholder. Epoxy 10 is introduced into the capsule under increasing pressure. Preferably, hydrostatic pressure and impregnation pressure are increased simultaneously until the impregnation pressure reaches 1500 psi and the desired net overburden pressure is reached. Such goal pressures are then preferably held for several minutes. The desired net overburden pressure may be, for example, an overburden pressure approximating that naturally occurring in the portion of the reservoir from which the samples were taken; or it may be such other pressure as is typically used with the particular coreholder in use or as is otherwise desired for the analysis of the core samples. Fluorescent dye Rhodamine B, or other dye, and any appropriate catalyst associated with such dye, may be added to the epoxy 10 prior to introducing the epoxy into capsule 8.

After introduction of the epoxy into the capsule is complete, the chamber of the coreholder comprising the capsule is isolated, as by closing ball valves 11. The chamber is maintained under pressure for several hours or until the epoxy introduced into the capsule becomes hardened. When the hard epoxy resin is formed, the capsule will be hardened. The hardened capsule may then be removed from the coreholder, and the heat shrink tubing may be cut away. The capsule may then be cut or ground longitudinally through the sand 12 until the boundaries of the stack of plugs and highly porous material or filtrose can be seen. Cuts may then be made through the highly porous material 2 to separate the plugs 1 or core samples from such material 2. Thin sections of the core samples may then be made using known methods.

What is claimed is:

1. A method of impregnating core samples with a resin, comprising:
   stacking the core samples with layers of permeable material between the samples and at each end of the stack;
   encasing the stack with a jacket of a permeable material;
   forcing a liqueform, resin-former into the stack under a pressure and in a volume sufficient to flow through the jacket and layers of permeable material to impregnate the core samples; and
   form the resin within the core samples.

2. The method of claim 1 which further comprises pressurizing the exterior of the jacket while forcing the resin-former into the stack.

3. The method of claim 1 wherein the resin-former is an epoxy.

4. A method for impregnating core samples with epoxy resin comprising:
   obtaining at least two core samples;
   stacking said core samples alternately with highly permeable material;
   positioning said stack in heat shrink tubing, with highly permeable material at both ends of the stack and with coarse sand between the outer walls of the stack and the inner walls of the tubing;
   heat shrinking said tubing around said stack;
   positioning said stack in a coreholder;
   introducing epoxy into said stack under increasing pressure;
   hardening said epoxy to form an epoxy resin in said stack; and
   removing said stack from the coreholder.

5. The method of claim 4 wherein said epoxy contains a dye.

6. The method of claim 5 wherein said dye is a fluorescent dye.

7. The method of claim 4 wherein said highly permeable material is comprised of silica sand and aluminum silica glass.

8. The method of claim 4 wherein said coreholder is an overburden coreholder.

9. The method of claim 4 wherein said coreholder is an overburden coreholder capable of having hydrostatic overburden pressure applied to it, and said stack is evacuated under vacuum and hydrostatic pressure is applied to the coreholder before said epoxy is introduced, and wherein the hydrostatic pressure and impregnation pressure are increased concomitantly after introduction of the epoxy into the stack until the impregnation pressure reaches 1500 psi and the desired net overburden pressure is reached at which time said pressures are held for several minutes.

10. The method of claim 4 further comprising after removing said stack from said coreholder:
    cutting away the heat shrunk tubing from the stack and removing the sand from the outer portion of said stack to expose the boundaries of the core samples and the highly permeable material; and
    separating said core samples from said permeable material.

11. The method of claim 4 wherein the stack is wrapped in paper before the stack is positioned in the heat shrink tubing and said paper is removed before the heat shrinking of said tubing.

12. The method of claim 4 wherein said core samples are taken from unconsolidated sands.

* * * * *